United States Patent
Zeoli et al.

(10) Patent No.: US 7,578,806 B2
(45) Date of Patent: Aug. 25, 2009

(54) DISPOSABLE SYRINGE WITH RETRACTILE NEEDLE

(75) Inventors: Filomena Zeoli, Sepino (IT); Mario Sozio, Latina (IT)

(73) Assignee: Filomena Zeoli, Sepino (CB) (IT)

( * ) Notice: Subject to any disclaimer, the term of this patent is extended or adjusted under 35 U.S.C. 154(b) by 206 days.

(21) Appl. No.: 10/534,866

(22) PCT Filed: Jul. 10, 2003

(86) PCT No.: PCT/IT03/00435
§ 371 (c)(1), (2), (4) Date: Oct. 31, 2005

(87) PCT Pub. No.: WO2004/043523
PCT Pub. Date: May 27, 2004

(65) Prior Publication Data
US 2006/0167410 A1    Jul. 27, 2006

(30) Foreign Application Priority Data
Nov. 12, 2002   (IT) .......................... CB2002A0005

(51) Int. Cl.
A61M 5/32   (2006.01)
(52) U.S. Cl. ........................... 604/195; 604/110

(58) Field of Classification Search ............... 604/110, 604/187, 111, 195, 197, 198, 93.01
See application file for complete search history.

(56) References Cited

U.S. PATENT DOCUMENTS

| 5,114,410 | A | * | 5/1992 | Caralt Batlle | ............... 604/195 |
| 5,376,080 | A | * | 12/1994 | Petrussa | ..................... 604/198 |
| 5,407,436 | A | * | 4/1995 | Toft et al. | ................... 604/195 |
| 5,487,732 | A | | 1/1996 | Jeffrey | |
| 5,853,390 | A | | 12/1998 | Freschi | |

FOREIGN PATENT DOCUMENTS

| WO | WO 00/64515 | 11/2000 |
| WO | WO 01/47588 | 7/2001 |

* cited by examiner

Primary Examiner—Nicholas D Lucchesi
Assistant Examiner—Christopher D Koharski
(74) Attorney, Agent, or Firm—Young & Thompson

(57) ABSTRACT

A disposable syringe having a double hook element (9), causing, after a piston stroke toward the end of the socket element (4) of the needle, allowing retraction within the reservoir (1) during the reverse stroke of the piston (2). A spring (8) between the double hook element (9) and the end of a reservoir lip, when compressed, maintains the double hook element (9) in its position, and when extended, acts to cause the return of the needle (5) within the reservoir (1).

4 Claims, 5 Drawing Sheets

DISPOSABLE SYRINGE WITH RETRACTILE NEEDLE

The present invention relates to a disposable syringe with retractile needle.

More specifically, the invention concerns a syringe of the above kind provided with a needle retractile in such a way to prevent a second use of the same.

As it is well known, there are already available on the market different kind of syringes on which the needle is applied from outside on the body of the reservoir of the syringe by the coupling with a plastic support or socket.

After the use, said needle is usually disposed along with the syringe, very often without any protection of the suitable cap.

It is well evident that disposal of the syringe in this way involves the risk of transmitting diseases by contacting the needle, transmission that can occur in case of using the syringe by more than one user, or puncture during the positioning of the protection cap on the needle, or of occasional contact with the needle by those in charge of cleaning the place where the syringe has been thrown away without using the cap to protect the needle.

In view of the above, different solutions have been studied in the past in order to solve the above drawback.

However, none of the suggested solutions allows to solve in a definitive way the above mentioned drawbacks, since each of them introduces a remarkable use complexity, it being necessary to use them with a different procedure with respect to that of the traditional disposable syringes.

Furthermore, reduced dimensions and the number of single pieces comprising the syringes make production complicated.

Among the various solutions suggested there can be mentioned the solutions providing the rotation of the piston in such a way as to release the needle from its seat and pulling it away by the same piston, or those providing the piston with hooks that at the end of the stroke can block the needle, hooking on the same, and withdrawing the same during the following ascent phase of the piston.

However, each one of the above mentioned solutions is such as to induce a series of consequences, among are which the premature exit of the needle during an injection, or a recoil or steps that could jeopardise the functionality of the device.

In view of the above, the Applicant has realised a disposable syringe able to solve all the above mentioned drawbacks.

Main object of the present invention is therefore that of providing a syringe that is easy to be used and simple to realise.

Still another object of the present invention is that of providing a disposable syringe that is irreversible, so that, once passed the activation limit, determining the complete use of the syringe contents, and in any case allowing mixing of medicines before the injection, and the sureness of activating the syringe, the same syringe can no more be used.

A further object of the present invention is a disposable syringe that is stable, i.e. realised in such a way to prevent steps and recoil during its use.

Still another object of the present invention is that of providing a syringe that is cheap and easy to be realised, being comprised of a very low number of pieces to be assembled.

It is a further object of the present invention to provide a syringe of the above kind that is very easy to be used, not being required by the user any further procedure but to pay attention not to pass the irreversibility limit, indicated and viewable on the body of the syringe before its use.

Therefore, a specific object of the present invention is a disposable syringe with retractile needle, comprising a reservoir, having a rear end open for the slidable insertion of a piston element, provided with a gasket on the end facing the inside of said reservoir, and a front end, open as well, provided with lip for the shielding of a needle, and a protection cap for the needle when it is not used, said syringe being characterised in that it is provided a needle carrier socket element, coupable with said lip of the reservoir from inside the same reservoir, in that a seat is realised on said lip for seating a sealing gasket between needle carrier socket and reservoir lip, in that it is provided a double hook element, causing, after the piston stroke toward the end of said socket element of the needle, to allow its retraction within the reservoir during the reverse stroke of the piston, and in that an elastic element or spring is provided between said double hook element and the end of said reservoir lip, that, when compressed, maintains said double hook element in its position, and when extended, acts to cause the return of the needle within the reservoir.

According to the invention, an irreversibility point is indicated on said reservoir, indicating the irreversibility of the piston action.

Always according to the invention, said socket element for the needle provides a hinge for spherical coupling of the double hook element, a start for the translation of the socket element from the seat, a seat for the fixed joint of a lug of the double hook element, a stop for said double hook element, a seat for said elastic element or spring, a seat for said sealing gasket between socket and syringe body, a seat having a conical start for said needle, and walls having reduced tolerance.

Always according to the invention, said double hook element provides a hollow cylinder, provided with large longitudinal cuts on its upper part, lateral lugs, coupled with said central cylindrical body, and symmetrically provided with respect to the same, coupling with a "knee" seat realised on said socket element, and its end provided according to a reduced angle hinge, allowing only a partial rotation about its axis, and, at the bottom, with lugs, said lugs being provided with an irreversible hooking with said needle carrier socket.

Preferably, it is provided a plurality of lateral lugs on the double hook element.

Still according to the invention, it can be provided a plurality of elastic elements or springs, placed in series.

According to the invention, said piston can have each shape.

Furthermore, according to the invention, said double hook element can be coupled with the needle carrier socket by welding or fixed joint.

Still according to the invention, said needle carrier socket element remains blocked, with respect to the downward vertical movements, by a force coupling with said sealing gasket, and by the suitable seat realised in said lip syringe, with respect to the upward vertical movements by said lugs of the double hook element, engaging on the syringe body in a suitable seat, with respect to the transverse movements, by the coupling with minimum tolerances between socket element and syringe body, and with respect to the rotation movements about the syringe axis by friction.

Always according to the invention, said elastic element or spring and said sealing gasket are compressed during the injection phase, contributing to maintain said double hook element in position, pushing it upward against the syringe body.

Always according to the invention, said piston, passing said irreversibility point, arms the hooking device of the double hook element, causing the buckling by rotation of the lateral lugs, thus releasing said "knee" element from the restraint with the syringe body, and said double hook element, sliding downward, by lugs provided with fixed joints, hooks on the needle carrier socket element, thus realising a sole assembly wit the same socket element, needle—needle carrier socket element—double hook element assembly sliding backward by the action of the elastic element or spring, dragging, in its extension stroke said needle within the reservoir, released by the pushing action on the piston.

Preferably, the elements comprising the syringe according to the invention are comprised of deformable material.

The present invention will be now described, for illustrative but not limitative purposes, according to its preferred embodiments, with particular reference to the figures of the enclosed drawings, wherein.

Figure 1:
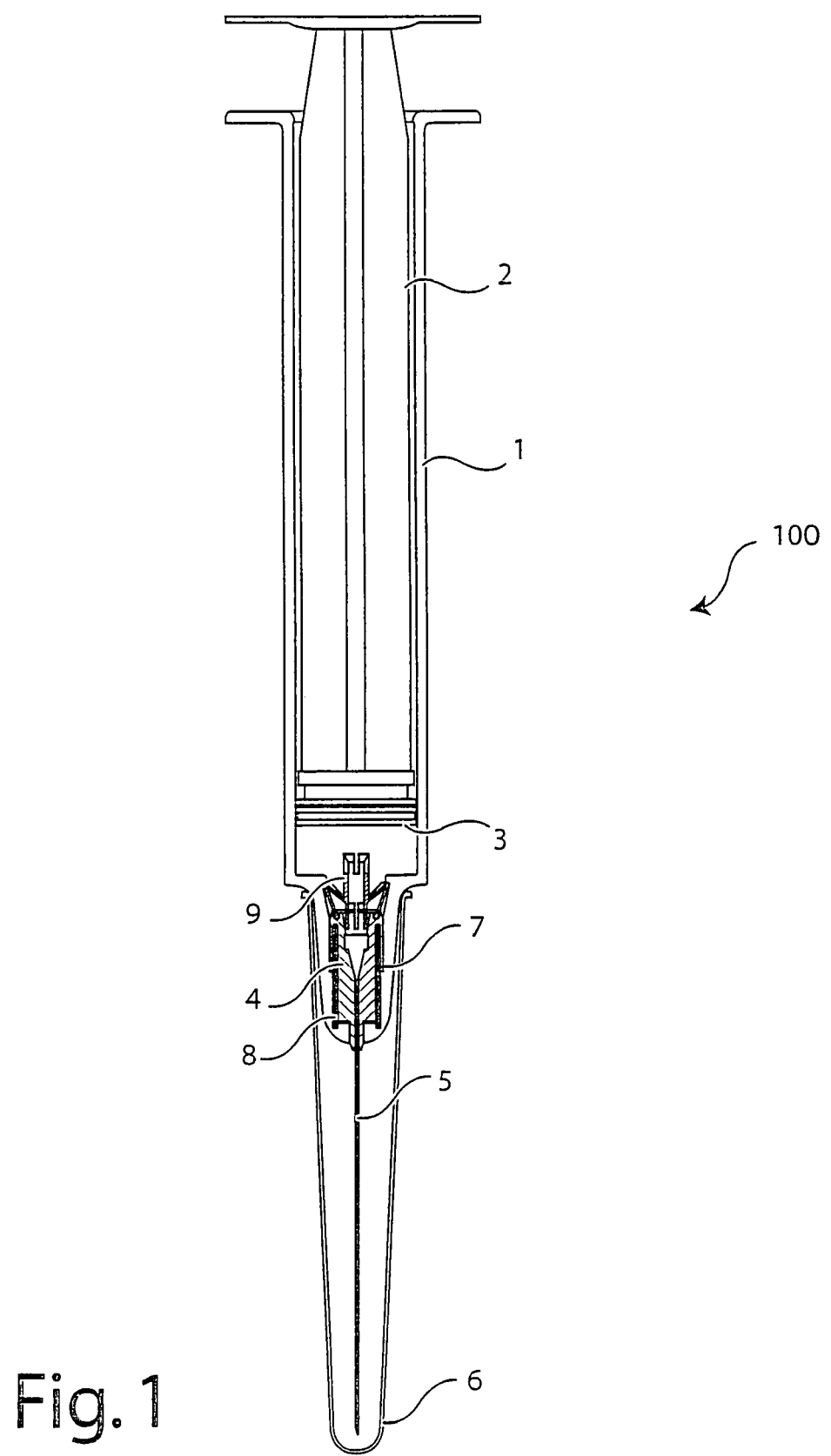
FIG. 1 is a view, partially in section, of a disposable syringe according to the invention.

Coming now to observe all the figures of the enclosed drawings, a syringe according to the invention, generically indicated by reference number 100, provides the following components, which are present also in the standard syringes already available on the market, namely a cylindrical reservoir 1, a piston 2, a sealing gasket 3 for the piston 2, a socket 4 for engagement of the steel needle 5, and a cap 6, for the protection of the needle 5 before and after the use of the syringe 100.

Syringe 100 according to the present invention provides three additional elements, namely a sealing gasket 7, a spring 8 and a double hook element 9, that in the following will also be indicated as spider element, said elements, and their functionality, being described in greater detail in the following.

As it will be clearly noted from the following description, syringe 100 according to the invention allows to mix the substances to be injected, making an injection, and sucking blood.

The structure of the syringe 100 according to the invention provides its use without releasing the needle retraction device, and the triggering of the mechanism, making the use of the needle irreversible.

Coming now to observe in greater detail the various figures enclosed, the innovative parts of the syringe 100 according to the invention will be described.

Reservoir 1 of the syringe 100 according to the invention is, as in the standard syringes, but the lip including the needle 5 from inside and not from outside.

Figure 2:
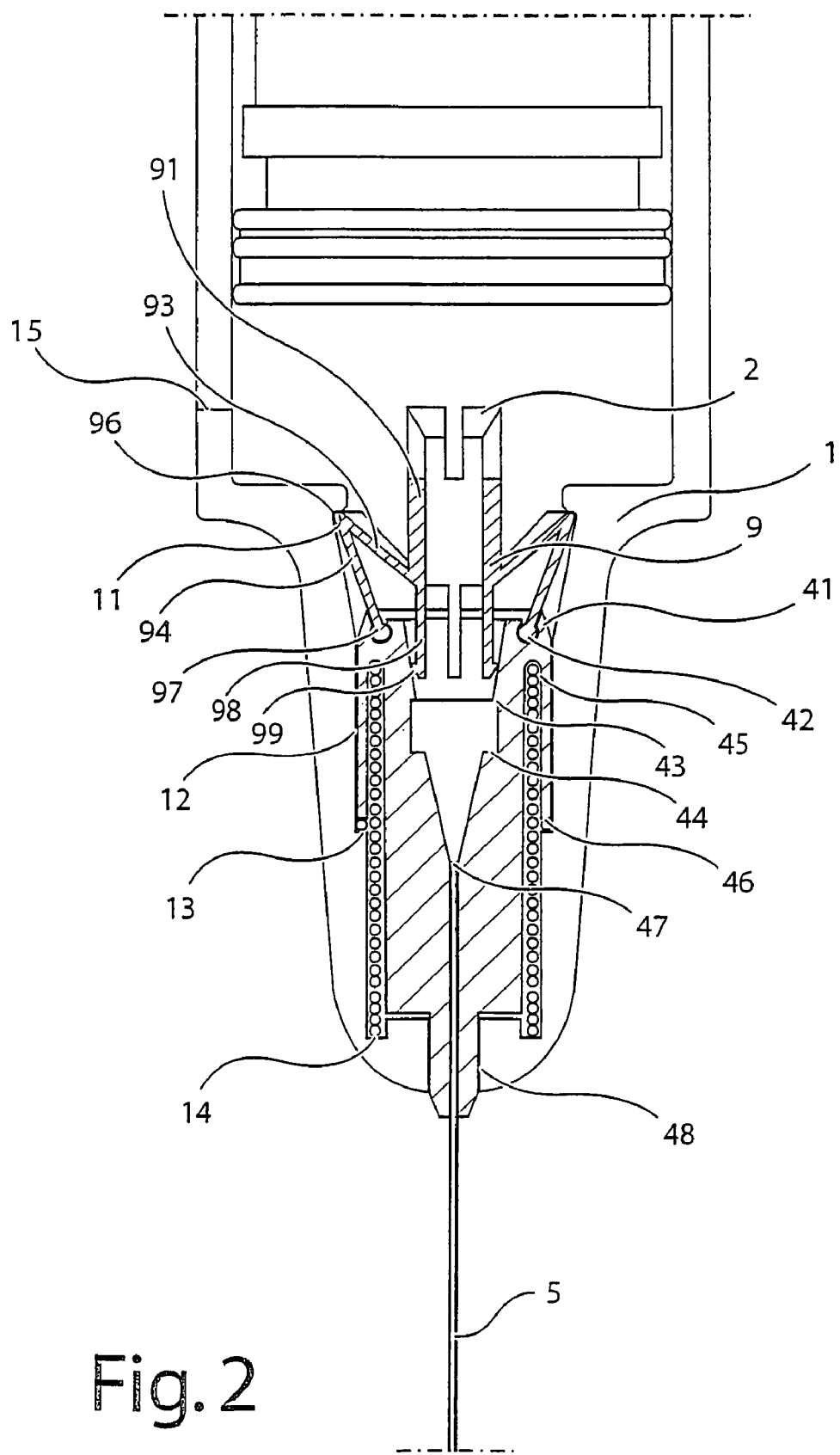
FIG. 2 is a view, partially in section, of a particular of the disposable syringe of FIG. 1.

Particularly, as it can be clearly noted from FIG. 2, said lip of the reservoir 1 has an outer rounded shape, and provides an anchoring seat 11 for the double hook 9, walls 12 with a reduced tolerance to receive the needle 5 carrier socket 4, a seat for the sealing gasket 7, a seat 14 for the spring 8, as well as an indication 15 of the irreversibility point.

As to the piston 2, it is identical to the one used for the standard syringes with a flat bottom. The gasket 3 too for the seal of the piston 2 is identical to the one used for the standard flat bottom syringes.

Figure 4:
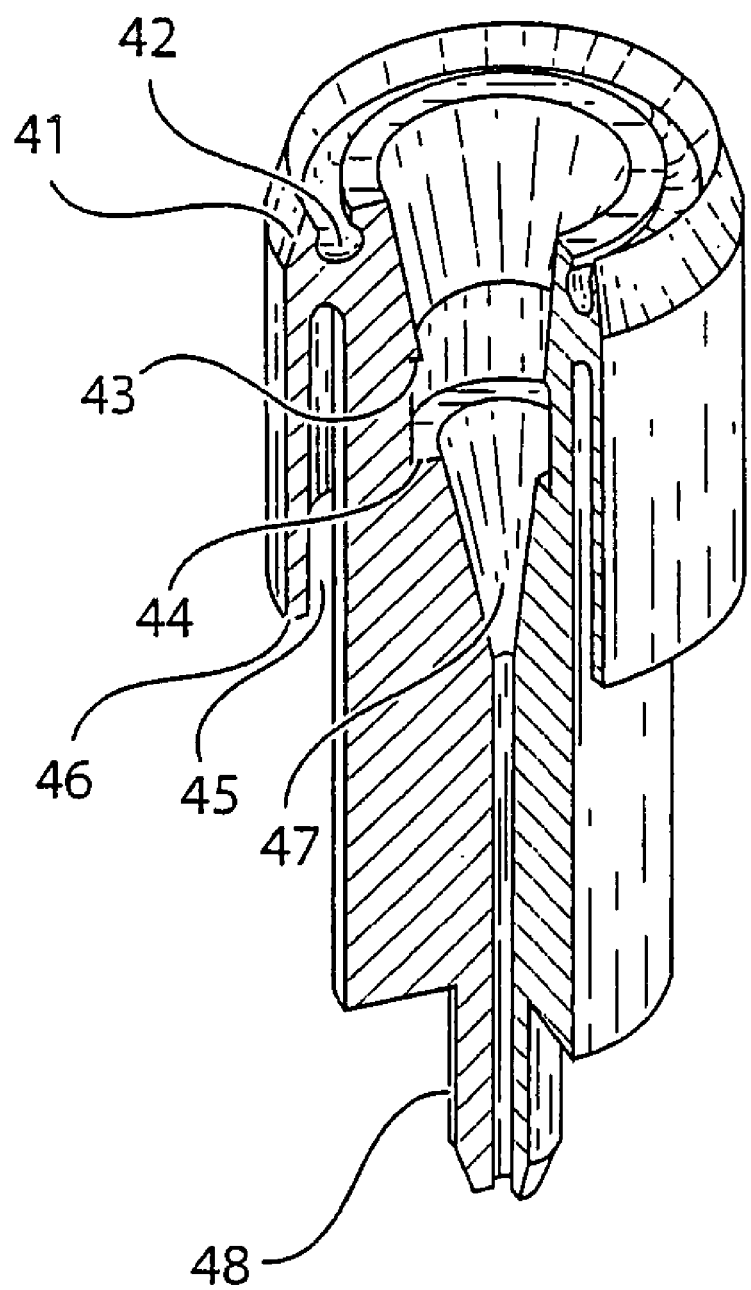
FIG. 4 is a detailed perspective tridimensional view, partially cut away, of the needle carrier socket of the syringe shown in the preceding figures.

Observing now the needle 5 socket 4 (see also the enclosed FIG. 4), it is one of the main innovative features of the solution suggested according to the present invention. First of all, said socket 4 is mounted inside the reservoir 1, rather than outside, as in the standard syringes.

Said socket 4 (see in particular FIG. 2) provides a hinge 41, for the spherical coupling of the double hook element 9, a beginning 42 for the translation of the seat of the socket 4, a seat 43 for the fixed joint of the lug of the double hook element 9, a stop of the double hook element 9, a seat for the spring 8, a seat 46 for the sealing gasket between socket 4 and syringe 100 body 1, a seat 47, with a conical start for coupling the needle 5, and walls having reduced tolerances with respect to the syringe 100 body 1.

The needle 5 too is substantially identical to the traditional ones, and is mounted on said socket 4.

As to the cap 6, it is substantially identical to the traditional ones, being characterised by a wider conicity, since the lip has bigger dimensions with respect to a traditional cap. Positioning of the cap 6 is in any case obtained by a simple pressure on the lip.

Sealing gasket 7 suggested according to the present invention is indispensable to prevent or minimize leakage of liquid contained within the syringe 100 during the injection. The presence of this gasket, comprised of a rubber ring, between the syringe 100 body 1 has a remarkable importance. It is provided between the lip of the body and the needle 5 carrier socket 4, specifically shaped to receive said element.

As to the spring 8, it is provided to allow to the needle 5 to be retracted within the reservoir 1. Said spring 8 is housed within a seat partially obtained in the lip of the syringe 100 body 1 in the needle 5 carrier socket 4.

Figure 5:
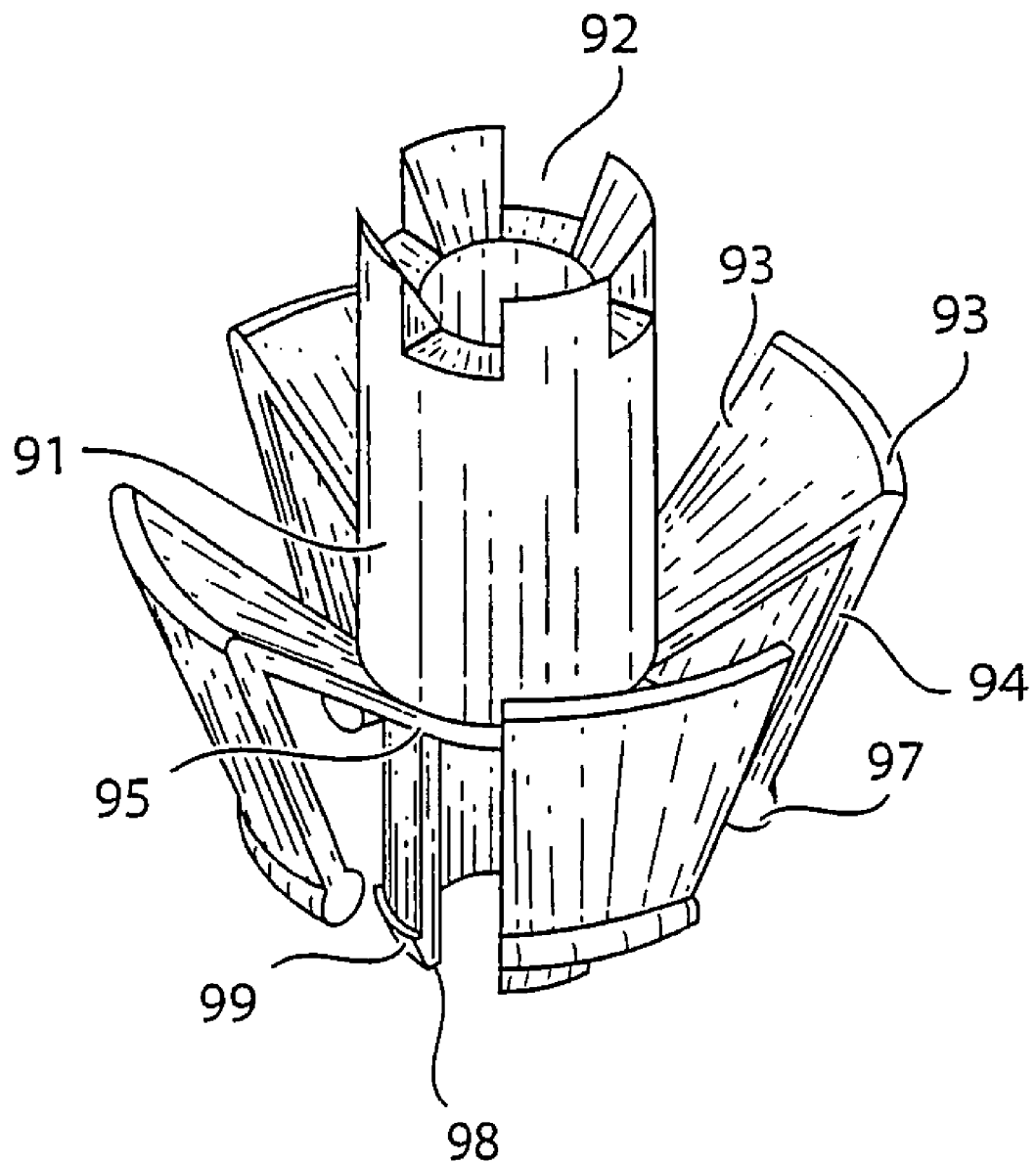
FIG. 5 is a detailed perspective tridimensional view, partially cut away, of the double hook element of the syringe shown in the preceding figures.

Coming now to describe in greater detail the double hook element 9, and observing also FIG. 5, it comprises, along with the needle 5 carrier socket 4, the greatest novelty introduced according to the invention.

It is a complex geometry element, providing a hollow cylinder 91, having large longitudinal cuts 92, realised in the upper part, and lateral lugs 93, 94, joined with the cylindrical central body 91 in correspondence of the point indicated by the reference number 95 and provided symmetrically with respect to the cylindrical body 91.

Said lugs 93, 94, if seen in section, can be schematised as two rods 93, 94 fixed within a "knee" 96, and with the ends 97 in a reduced angle hinge realised on the socket 4, only partially allowing the rotation about its axis.

Two further lugs 98 are provided, symmetric with respect to the cylindrical body 91, and provided with ends 99 for irreversible hooking with the needle 5 carrier socket 4.

In the following, the operation of the syringe 100 according to the present invention will be described, it being thus possible to put into evidence all the innovative features introduced.

Needle 5 carrier socket 4 is placed within the syringe 100, and remains blocked with respect to every movement. Particularly, vertical downward movements of the socket 4 are prevented by the force coupling between the rubber sealing gasket 7 and the suitable seat 13 obtained in the lip of the syringe 100, while upward vertical movements are prevented by the lugs of the double hook element 9, abutting on the syringe 100 body in the suitable seat 11.

As to the transverse movements of the socket 4, restraint is comprised of the socket 4—syringe 100 body 1 coupling providing minimum tolerances, while rotation movements about syringe axis 100 are prevented by the friction of the force torque between syringe 100 body 1 and the knee 96 of the double hook element 9.

Spring 8 and sealing gasket 7 are compressed and contribute to maintain in position the double hook element 9, pushing it upward against the syringe 100 body 1, in correspondence of said seat 11.

During the injection, piston 2 moves toward the bottom; once passed the irreversibility point 15, indicated on the reservoir 1 by a viewable mark, piston 2 acts in such a way to arm the hooking device 99, and at the same time acts on the double hook element 9, pushing it downward.

Said push causes deformation of the lateral lugs 93, 94, releasing the knee 96 from the seat 11 realised in the syringe 100 body 1. Sliding downward, double hook element 9, with the lugs 98, along with the fixed joint elements 99, hooks with the needle 5 carrier socket 4 in correspondence of the coupling seat 43, thus realising a single assembly with the same socket 4.

Said operation is irreversible, so that it will no more be possible to bring the double hook element 9 in the start conditions.

The assembly comprised of needle 5, needle 5 carrier socket 4 and double hook element 9 slides backward by the action of the spring 8, that is allowed to decompress, dragging the needle 5 with the lip.

Spring 8 action acts also on the piston 2, so that the same goes back, leaving free a space within the reservoir 1 to receive the needle 5.

Figure 3:
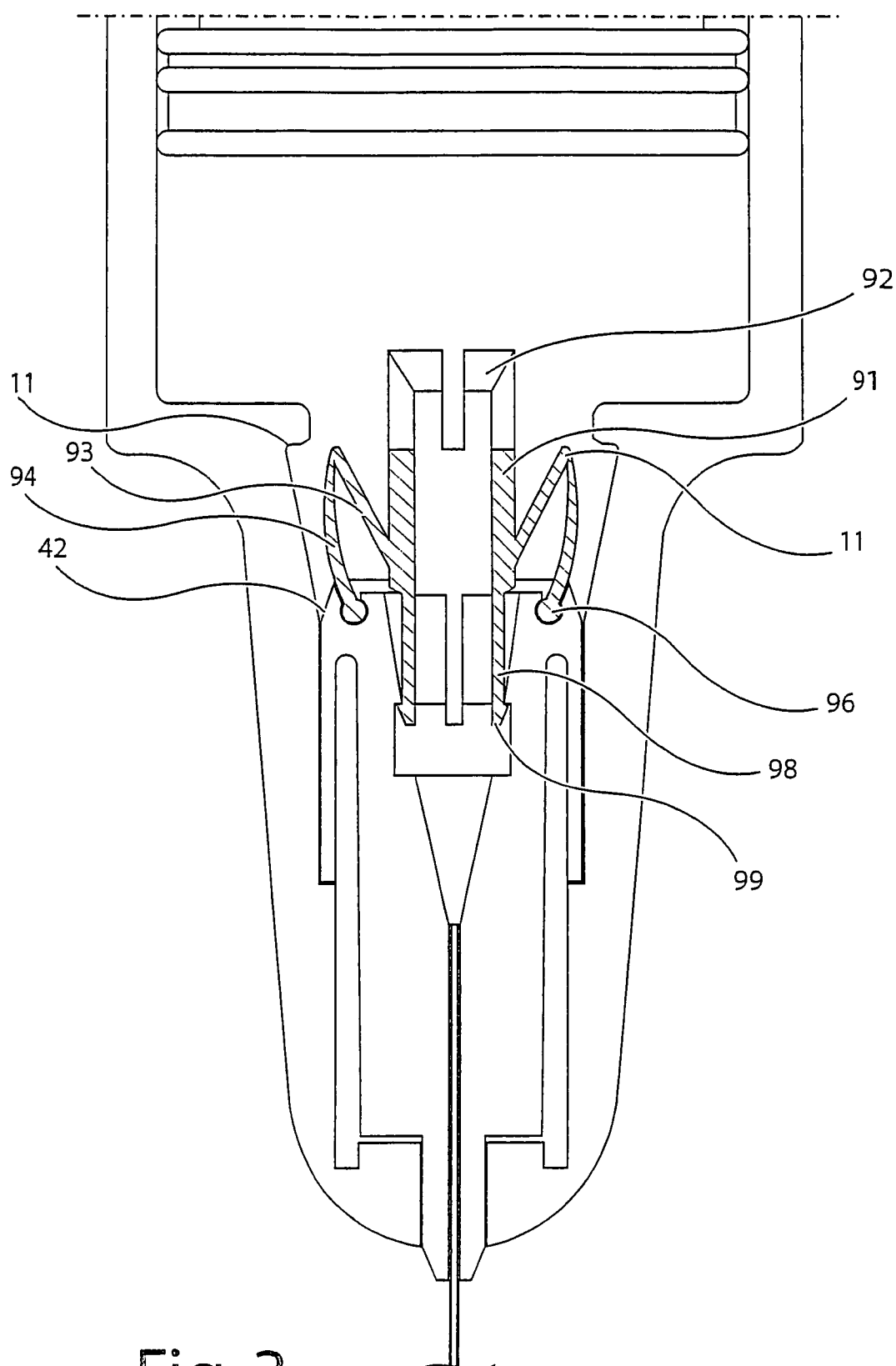
FIG. 3 is a view, partially in section, even more in detail, of the particular of FIG. 2.

FIG. 3 shows in section the lip of the reservoir 1, putting into evidence the needle 5 socket 4, the double hook element 9, in armed position, the spring 8 and the compressed sealing gasket 7. Piston 2 thrust makes it possible the deformation by rotation of the lateral lugs 93, 94, releasing the knee 96 from the seat 11 realised in the syringe 100 body 1. Sliding downward, double hook element 9, by the lugs 98 provided with fixed joint elements 99, hooks the needle 5 carrier socket 4 in correspondence of the seat 43, thus realising a sole assembly with the same socket 4.

The present invention has been described for illustrative but not limitative purposes, according to its preferred embodiments, but it is to be understood that modifications and/or changes can be introduced by those skilled in the art without departing from the relevant scope as defined in the enclosed claims.

The invention claimed is:

1. A syringe with a retractable needle, comprising a reservoir having an open rear end, a piston element slidably inserted in said rear end, the piston having an end facing toward the inside of the reservoir, the reservoir having a front end open and surrounded by a lip, a needle carrier carrying said needle and slidable in said lip toward and away from said piston, a spring within the lip continuously urging the needle carrier toward the piston, an inwardly extending shoulder on the lip, an inwardly extending shoulder on the needle carrier, and a flexible element secured to and movable with the needle carrier, said flexible element having portions that engage with said shoulder on the lip when the spring urges the needle carrier toward the piston thereby to limit movement of the needle carrier toward the piston, said flexible element having a member thereon engageable by the piston to press a portion of the flexible element into the needle carrier, said portion of the flexible element having hooks thereon that, when pressed into the needle carrier, engage beneath the shoulder on the needle carrier to retain the flexible element in a deformed position in which the needle carrier is deformed out of contact with the shoulder on the lip, whereupon, when the piston is retracted in a direction away from the needle, the spring can press the needle carrier and the needle and the deformable element in a direction toward the piston thereby to retract the needle within the lip, said flexible member having a plurality of lateral lugs thereon of V-shaped configuration with each having an apex, said apex of the V being the portion of the flexible member that engages beneath the shoulder on the lip.

2. A syringe as claimed in claim 1, said flexible member being of single piece plastic construction.

3. A syringe as claimed in claim 1, one leg of each V shaped lug being secured to a central portion of the flexible member and another leg of the V-shaped lug being rotatably secured to the needle carrier.

4. A syringe as claimed in claim 1, said needle carrier having a second shoulder thereon facing the piston and limiting movement of a central portion of the flexible member toward the needle.

* * * * *

UNITED STATES PATENT AND TRADEMARK OFFICE
CERTIFICATE OF CORRECTION

PATENT NO. : 7,578,806 B2
APPLICATION NO. : 10/534866
DATED : August 25, 2009
INVENTOR(S) : Zeoli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 603 days.

Signed and Sealed this

Seventh Day of September, 2010

David J. Kappos
*Director of the United States Patent and Trademark Office*